(12) United States Patent
Evans

(10) Patent No.: US 8,226,699 B2
(45) Date of Patent: Jul. 24, 2012

(54) REUSABLE THERMAL PACK FOR THERAPEUTIC PURPOSES

(75) Inventor: Sharon Evans, New York, NY (US)

(73) Assignee: Snowflake Innovations, LLC, Wilmington, DE (US)

( * ) Notice: Subject to any disclaimer, the term of this patent is extended or adjusted under 35 U.S.C. 154(b) by 1015 days.

(21) Appl. No.: 12/172,152

(22) Filed: Jul. 11, 2008

(65) Prior Publication Data
US 2010/0010597 A1    Jan. 14, 2010

(51) Int. Cl.
*A61F 7/12* (2006.01)
*A61F 7/00* (2006.01)

(52) U.S. Cl. .......................... 607/114; 607/108; 607/109

(58) Field of Classification Search .................. 607/108, 607/109, 114
See application file for complete search history.

(56) References Cited

U.S. PATENT DOCUMENTS

| 5,393,462 A | 2/1995 | Avery |
| 2007/0083251 A1* | 4/2007 | von Hoffmann et al. ...... 607/114 |
| 2007/0197950 A1* | 8/2007 | Flick et al. ...................... 602/65 |

* cited by examiner

*Primary Examiner* — Nicholas Lucchesi
*Assistant Examiner* — Ian Holloway
(74) *Attorney, Agent, or Firm* — The Maxham Firm

(57) ABSTRACT

A flexible reusable thermal pack for therapeutic purposes. A flexible, insulative sealed pouch is partially filled with hollow balls containing freezable or heatable liquid and metal balls of substantial mass. The thermal pack slowly returns to ambient temperature while it conforms to be a body part needing therapeutic thermal treatment.

18 Claims, 2 Drawing Sheets

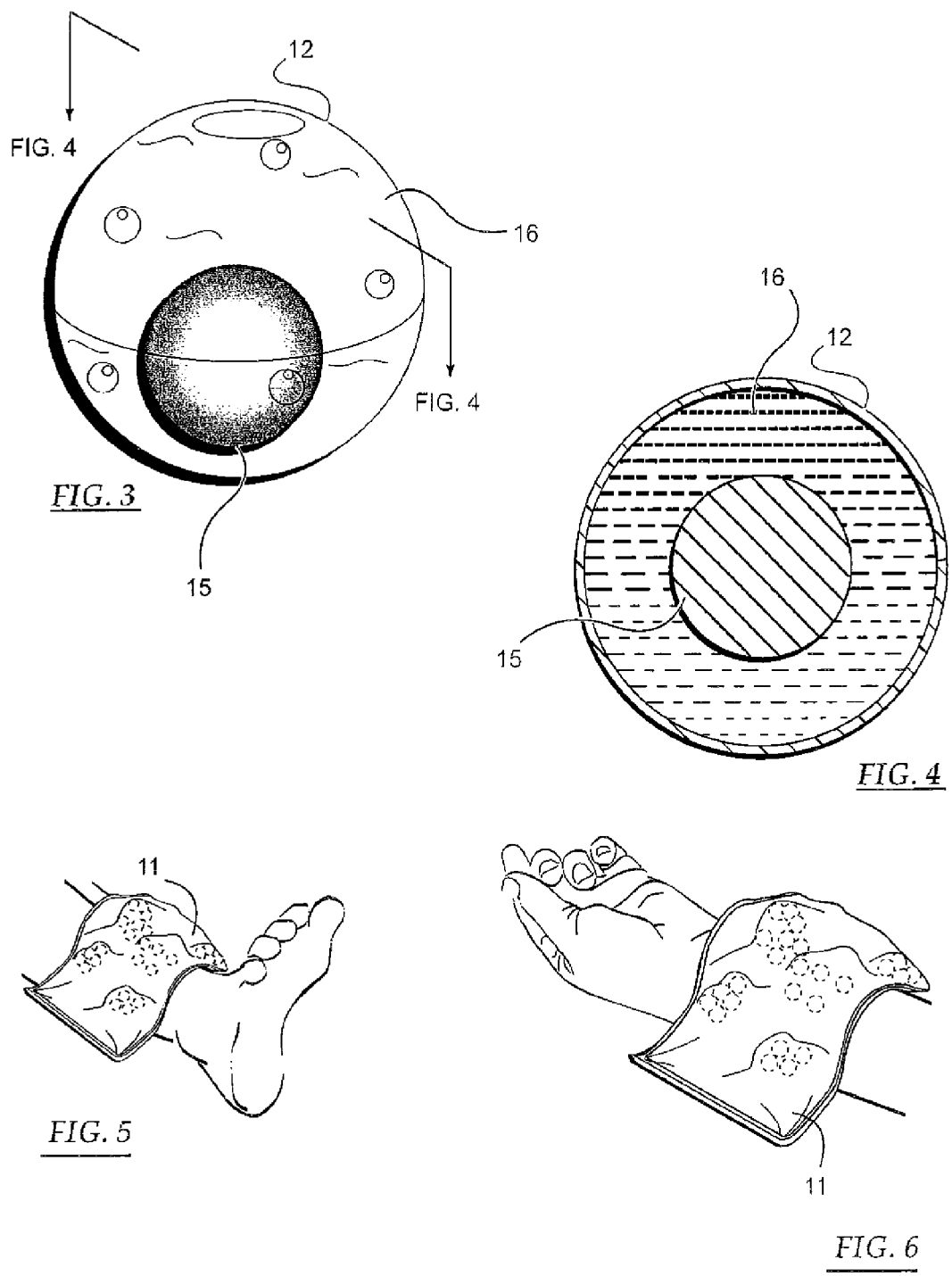

REUSABLE THERMAL PACK FOR THERAPEUTIC PURPOSES

FIELD OF THE INVENTION

This invention relates generally to thermal packs, and more particularly to ice packs for treatment of injuries of humans and animals.

DISCUSSION OF PRIOR ART

It is well recognized that injuries such as sprains and the like tend to respond favorably to the application of cold, often in the form of an ice pack. Some in the medical profession recommend use of a polyethylene bag of vegetables, for example, a "Pea pack." That is because even though the contents are frozen, they are flexible and readily conformed to the shape of the injured area of the body.

There are presently available devices for applying cold pressure to an injured area of the body. One is an old fashioned ice bag or pack, where ice cubes are put into some kind of flexible container and applied to the injury. Drawbacks include the need to have ice, which melts, leaving water residue that must be discarded and the ice replaced. Such ice packs often leak.

Another is a "blue ice" pack, which is most often used in an insulated container or bag. These are relatively rigid, are kept in the freezer, and are sealed. However, they often develop leaks after multiple uses. They are not flexible so they are typically used with a pad of some type when applied to the body to spread the cooling effect and to prevent an excess of cold temperature being applied to the body in a static manner.

Yet, another cold-applying device is a moldable, re-freezable-pack sold by P.I., Inc., of Athens, Tenn., under the trademark SOFTOUCH. It is the subject of U.S. Pat. No. 5,393,462.

SUMMARY OF THE INVENTION

A purpose of the invention is to provide a reusable, flexible and body part conformable, fully sealed thermal pack which readily conforms to the area of the human or animal body needing therapeutic attention. For sprains, for example, the healing process includes rest, ice, compression, and elevation (RICE). Various embodiments of this invention provide the ice and compression functions. Some injuries require heating rather than cooling.

In an exemplary embodiment, the invention comprises a sealed pouch being partially filled with relatively rigid plastic balls, each of which contains a solid metal ball which is smaller than the interior of the rigid plastic ball, and the plastic ball is otherwise filled with water or other freezable or heatable non-toxic liquid. The pouch may be round, oval, rectangular, and the like. The plastic balls are hollow and may have any shape, but generally oval, rounded, or spherical is preferred. The metal balls could be hollow but solid stainless steel is what is primarily contemplated. Other suitable metals may be used, and those metal balls may be coated for added anti-corrosion treatment.

BRIEF DESCRIPTION OF THE DRAWING

The objects, features, and advantages of the invention will be more readily perceived from the following detailed description, when read in conjunction with the accompanying drawing, wherein:

FIG. 3 is a see-through elevation of a plastic ball with a metal ball therein in accordance with the invention;

FIG. 4 is a cross section taken along cutting plane 4-4 of FIG. 3;

FIG. 5 is a partial perspective view showing the thermal pack of FIG. 1 applied to a person's ankle; and FIG. 6 is a partial perspective view showing the thermal pack of FIG. 1 applied to the person's wrist.

DETAILED DESCRIPTION OF THE PREFERRED EMBODIMENTS

An exemplary embodiment of the invention is shown in the attached drawing. It should be noted that the materials and parameters provided are by way of example only and the invention is not to be limited by these particulars. The description generally refers to use of the invention on humans, but it is equally applicable to animals.

Figure 1:
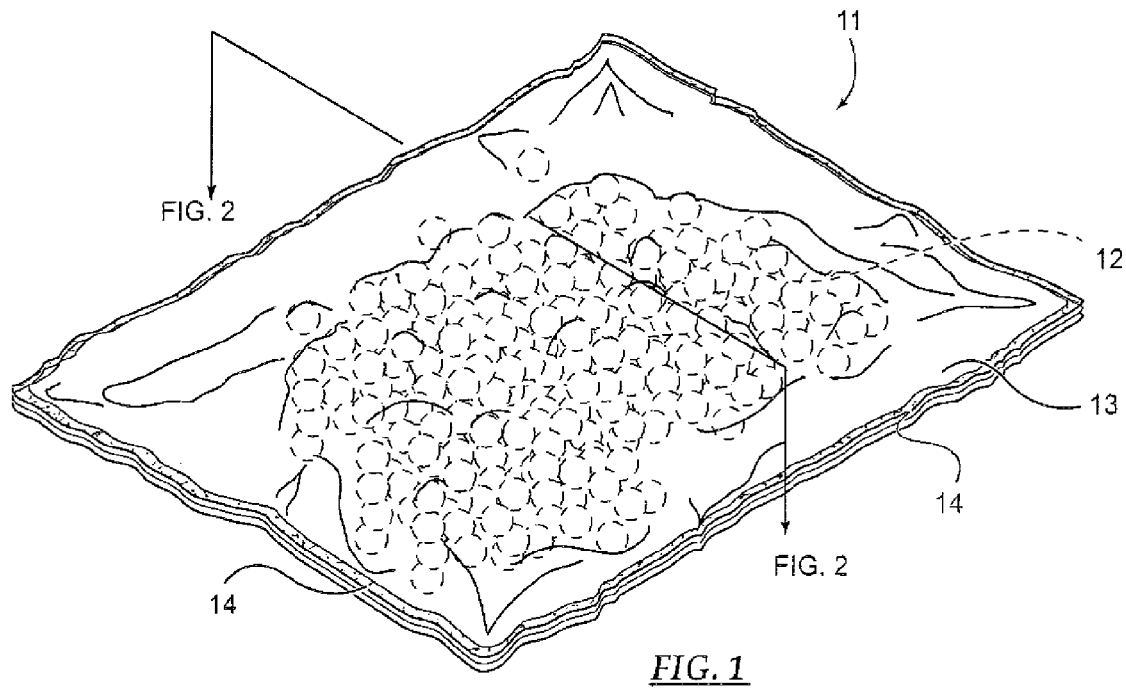
FIG. 1 is a perspective view of an embodiment of the thermal pack in accordance with the invention.
Figure 2:
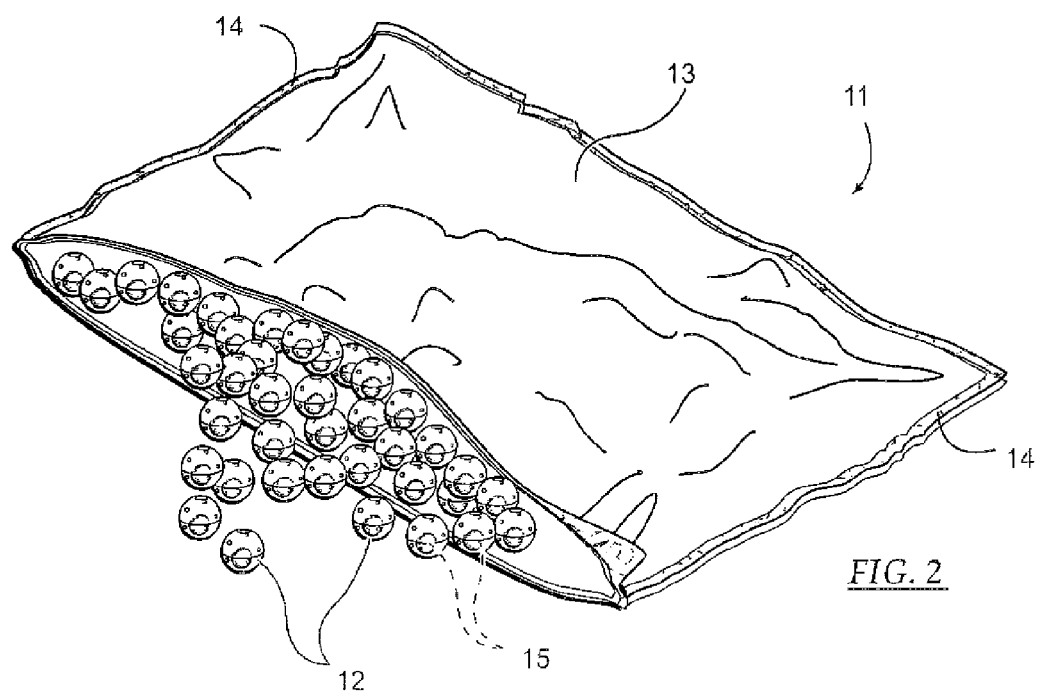
FIG. 2 is a cut away, perspective view, taken along cutting plane 2-2 of FIG. 1, of a thermal pack in accordance with the invention.

With reference now to the drawing, and more particularly to FIGS. 1 and 2, device 11 comprises pouch 13 having a plurality of plastic balls 12 occupying a significant portion of the interior of the pouch. Pouch 13 is sealed around edges 14 to make it leakproof. While device 11 will generally be referred to herein as a cool pack or an ice pack, it could also function as a heating pad or pack.

Pouch 13 is readily flexible, on the order of a frozen vegetable food package, peas, for example, to enable device 11 to readily conform to the body parts, such as those shown in FIGS. 5 and 6. The pouch material preferably includes a strong plastic layer, such as polyurethane of sufficient thickness and strength to resist inadvertent punctures. The pouch side panels and the edge seals are sufficiently strong to resist splitting, even as a person might sit on the device, at any normal temperature to which the pouch maybe subjected.

Inside the pouch are hollow plastic balls 12, each containing a metal ball 15, having an outside diameter substantially smaller than the inside diameter of the plastic ball. By way of example, plastic ball 12 may have an outside diameter of about 0.85 to about 1.55 inch, and an inside diameter of about 0.80 to about 1.50 inch. These measurements are general and are given only as examples.

The metal ball 15 is preferably solid and has an outside diameter of about 0.50 to about 0.80 inch. Again, these dimensions are for reference purposes only and could be substantially different. For example, for increased flexibility the plastic balls in the pouch could be made smaller, with commensurately smaller metal balls therein. For larger uses, possibly on a person's trunk (back, side, or stomach) or on a larger animal, the plastic balls, and the metal balls therein, could be larger than the specific example given.

While the term, "plastic," in relation to hollow balls 12, is used generically, any suitable material may be employed. Balls 12 should be relatively rigid, relatively strong so they are not readily crushable nor likely to break or split when even relatively severe pressure is applied, such as by a heavy person lying, sitting, or even kneeling on pouch 13. Examples of suitable materials for balls 12 include plastics, thick polyurethane, rubber, or any material the characteristics of which are not affected by liquids such as water, and by temperature change, including freezing and being heated to typical heating pad temperatures.

Examples of suitable materials for pouch 13 include aliphatic urethane, aromatic urethane, polyether urethane, and polyester urethane, among others. Its characteristics include flexibility and strength, as previously identified, providing a moisture barrier, being resistant to degradation from exposure to any light wavelength or to extreme heat, dryness, or humidity, or to body oils or hydrocarbons, and resistant to aging (oxidation). In order to achieve these characteristics, it may be necessary to make the pouch of two or more laminations. It could even have a thin protective coating or layer which only has a protective function, while the inner layer or layers provide the strength, toughness, and other desired characteristics. The inner layer may be an aluminum-coated material. Pouch 13 can desirably be made of a material which is slow to change temperature to ambient, that is, it can function as an insulative bag for either, or both, freezing and heating. Material from which the pouch maybe constructed can be purchased from the Carry Cool Company in Ft. Lauderdale, Fla.

Metal balls 15 are preferably solid stainless steel spheres. However, they could be hollow, and could be made of other metals or composites. The preferred characteristics are that balls 15 have significant weights or mass, and that they hold temperature for extended periods of time. There is no requirement that they be spherical. Balls 15 only need to be smaller than the interior diameter of hollow balls 12.

The space within balls 12 not occupied by metal balls 15 is substantially filled with a liquid 16, such as water. Since water can be frozen at 32° F., and requires increased calories to change from a frozen state to liquid state, it is a particularly suitable liquid for cold pack use. Any other liquid which holds temperature for an extended period of time would also be suitable. Preferably, liquid 16 is non-toxic so that no danger will result if one of hollow balls 12 is accidentally ruptured and if pouch 13 is ruptured.

As an integrated article, device 11 has significant weight and is flexible, so that it tends to press down by gravity, or drape over, the applied body part, as shown in FIGS. 5 and 6. Device 11, with its preferably insulative pouch 13, liquid 16 which stays cold or warm for extended periods of time, and metal balls 12 which also stay cold or warm for extended periods of time, provides an extremely versatile and effective ice pack that can be used for injury treatment purposes. It is preferred that the combination of pouch 13, liquid 16, and balls 12 will maintain a therapeutic temperature of a cold-pack or heating pad for up to, or at least about, three hours when cold, and generally somewhat shorter times when heated. One reason for having extended temperature maintenance is that a person may have more than one area of injury and maintaining low or increased temperatures enables the injured person to treat more than one area of the body without the need to get up and down to replace the therapeutic pack. Of course, when the term "maintain" is employed with respect to temperature, that does not mean there is no temperature change. There will be a gradual heating or cooling toward ambient as the time passes with the device in use. The thermal pack is typically employed on the injured area of the body for an extended period of time so that the person or animal tends to feel some aspect of relief or improvement, toward a comfort level.

What is claimed is:

1. A thermal pack for human or animal use, the thermal pack comprising:
    a flexible sealed pouch;
    a multiplicity of sealed plastic balls within said pouch;
    a metal ball within each said plastic ball, said metal ball occupying a portion of the space within said plastic ball; and
    a non-toxic, inert liquid occupying the remaining space within said plastic ball.

2. The thermal pack according to claim 1, wherein said pouch is made of temperature retaining material.

3. The thermal pack according to claim 2, wherein the thermal pack can selectively function as a cold pack and as a heating pack.

4. The thermal pack according to claim 3, where the thermal pack maintains a predetermined temperature for an extended period of time.

5. The thermal pack according to claim 3, wherein the thermal pack maintains a predetermined temperature for up to about three hours.

6. The thermal pack according to claim 3, wherein the thermal pack maintains a therapeutic temperature for at least three hours.

7. The thermal pack according to claim 1, wherein said metal balls are stainless steel.

8. The thermal pack according to claim 1, wherein said plastic balls are firm and substantially rigid.

9. The thermal pack according to claim 1, wherein said liquid in said plastic balls freezes when maintained at temperatures below the freezing point of said liquid.

10. The thermal pack according to claim 1, wherein said liquid freezes in a temperature range of below 32° F.

11. The thermal pack according to claim 1, wherein said liquid is water.

12. The thermal pack according to claim 1, wherein said multiplicity of plastic balls occupies about 65% to about 85% of the interior space of said pouch.

13. The thermal pack according to claim 1, wherein each plastic ball is about 0.8 to about 1.5 inch in interior diameter.

14. The thermal pack according to claim 1, wherein each said metal ball is about 0.5 to 0.8 inch in diameter.

15. The thermal pack according to claim 1, wherein said pouch is made of polyurethane.

16. The thermal pack according to claim 1, wherein each said metal ball is coated with a non-oxidizing material.

17. A method for thermally treating injuries to a living body, the method comprising:
    bringing a thermal pack to a therapeutic temperature, the thermal pack comprising a flexible sealed pouch, a multiplicity of sealed plastic balls within said pouch, a metal ball within each said plastic ball, said metal ball occupying a portion of the space within said plastic ball, and a non-toxic, inert liquid occupying the remaining space within said plastic ball; then applying the thermal pack to the injured area of the body.

18. The method according to claim 17, and further comprising maintaining the thermal pack on the injured area of the body for up to about three hours.

* * * * *